United States Patent [19]
Nash

[11] Patent Number: 5,149,322
[45] Date of Patent: Sep. 22, 1992

[54] MOTOR DRIVEN APPARATUS HAVING MEANS TO PREVENT REUSE AND METHOD OF USE OF SAID APPARATUS

[75] Inventor: John Nash, Dowington, Pa.

[73] Assignee: Kensey Nash Corporation, Exton, Pa.

[21] Appl. No.: 640,664

[22] Filed: Jan. 14, 1991

[51] Int. Cl.$^5$ .............................................. A61M 5/50
[52] U.S. Cl. ...................................... 604/110; 604/22
[58] Field of Search .................. 604/110, 22, 264, 280; 606/167–171

[56] References Cited

U.S. PATENT DOCUMENTS

| | | | |
|---|---|---|---|
| 3,597,582 | 8/1971 | Goode et al. | 604/110 X |
| 4,696,308 | 9/1987 | Meller et al. | 128/754 |
| 4,781,683 | 11/1988 | Wozniak et al. | 604/110 |
| 4,808,167 | 2/1989 | Mann et al. | 604/151 |
| 4,850,972 | 7/1989 | Schulman et al. | 604/151 |

Primary Examiner—John D. Yasko
Assistant Examiner—Adam J. Cermak
Attorney, Agent, or Firm—Caesar, Revise, Berstein, Cohen & Pokotilow, Ltd.

[57] ABSTRACT

A catheter instrument for effecting some minimally invasive medical procedure within the body of a living being. The instrument comprises an elongated tubular member, a working head, a rotary drive cable, and a drive disabling member. The tubular member is of small cross-sectional area to enable it to be inserted through a small opening in the body of the being. The working head is coupled to the drive means to be operated, e.g., rotated, thereby to effect some procedure adjacent its situs. The drive cable is coupled to a motor to efffect its rotation. The elongated member serves to carry a liquid, e.g. water, through at least a portion of it during the use of the instrument. The drive disabling member is responsive to the presence of liquid through the tubular member to change shape and/or size to prevent the drive cable from rotating some time after liquid is carried through the tubular member. This prevents further operation of said working head. In one embodiment the drive disabling member seizes the cable and in another embodiment it uncouples the cable from the motor.

23 Claims, 3 Drawing Sheets

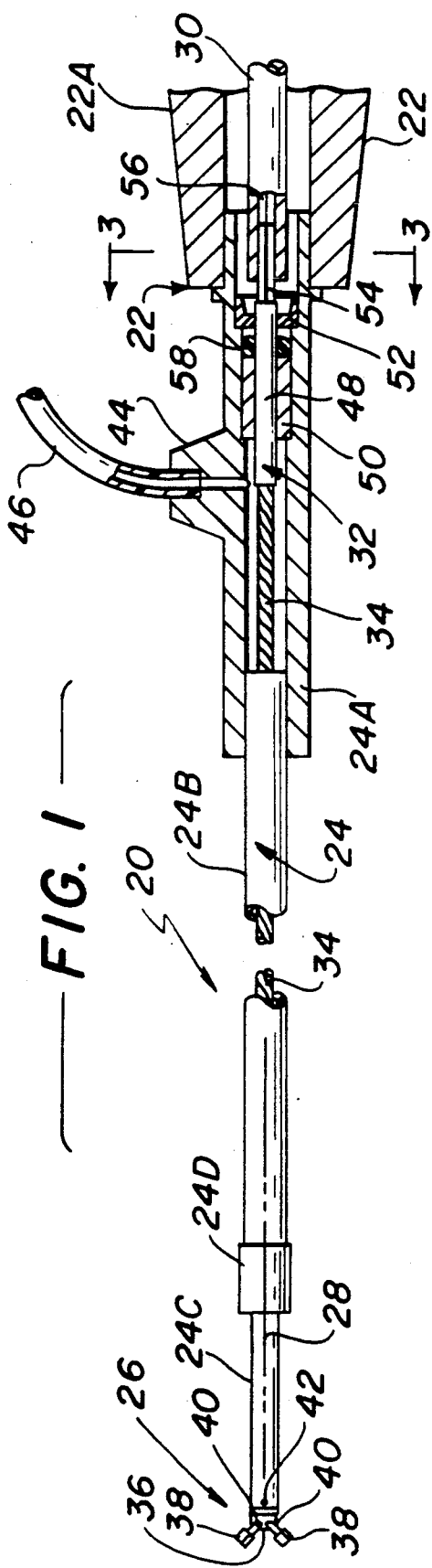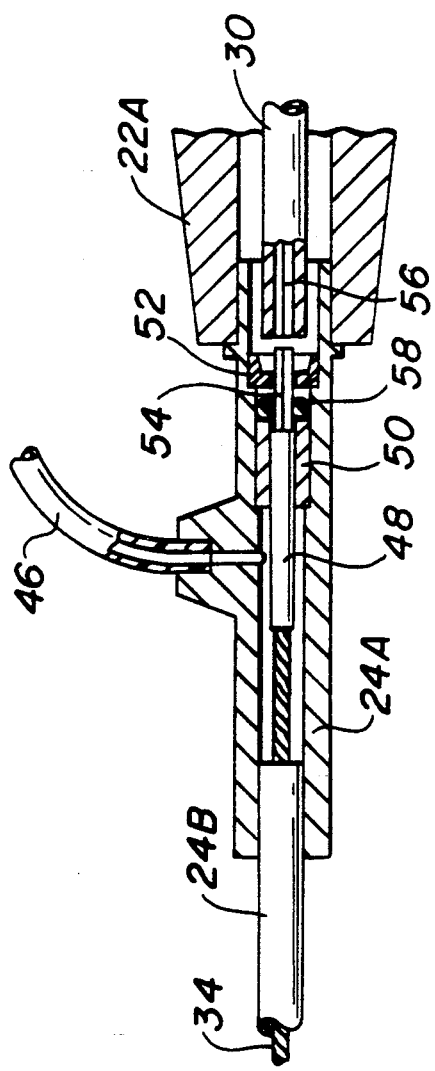

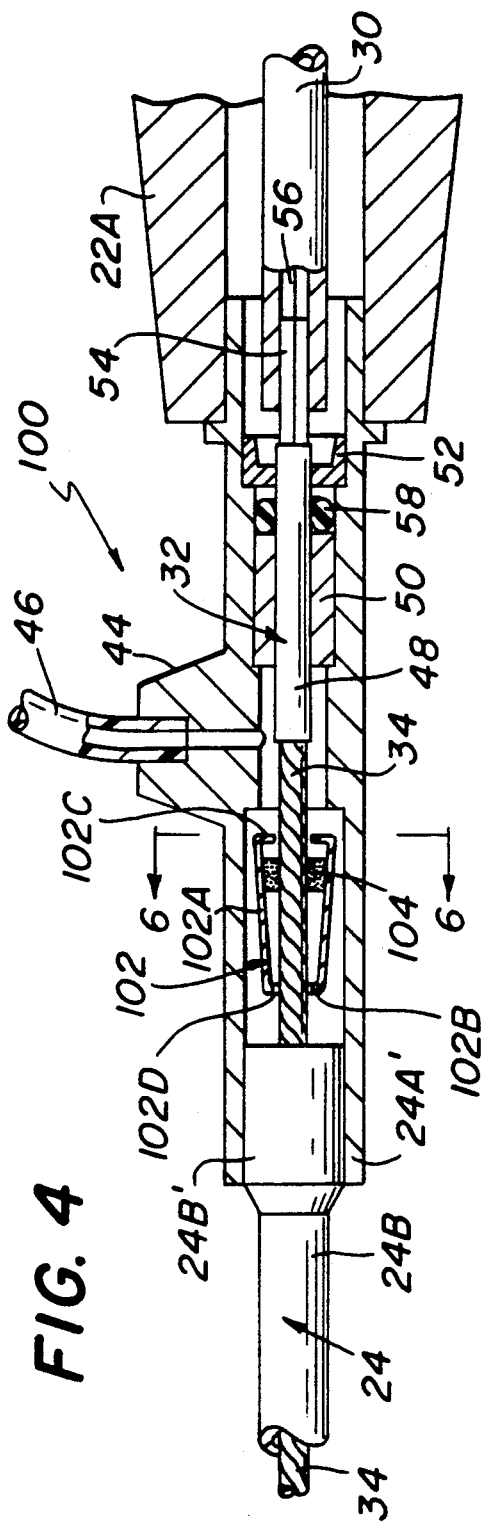
FIG. 4
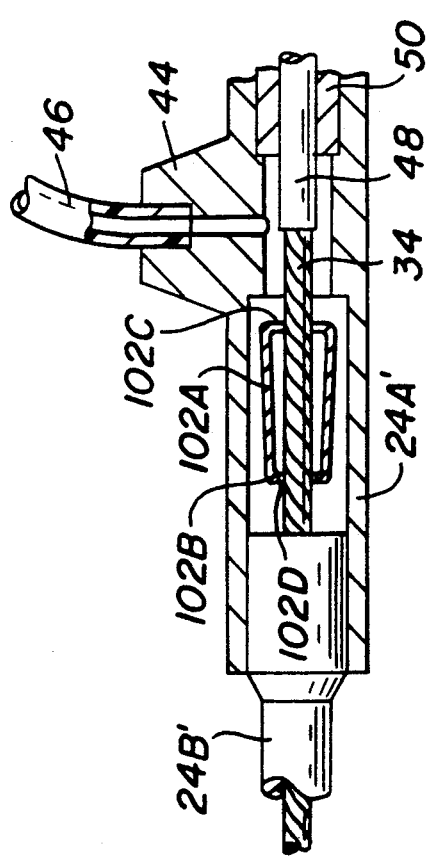
FIG. 6
FIG. 5

5,149,322

MOTOR DRIVEN APPARATUS HAVING MEANS TO PREVENT REUSE AND METHOD OF USE OF SAID APPARATUS

This invention relates generally to medical instruments and more particularly to catheter based instruments for effecting some procedure within the body of a living being.

BACKGROUND OF THE INVENTION

Medical instruments, such as catheters, are gaining wide acceptance in the medical community for effecting various procedures within the body of the patient which theretofore had been accomplished by general surgery. Those instruments have thus opened the way for what has become known as "non-invasive" surgery.

The destruction of stones, e.g., gallstones, kidney stones, etc., is one area in which non-invasive procedures are undergoing serious attention, and several patents and patent applications are directed to effecting such action via the use of a small instrument having a rotary working head arranged to be introduced into the body of the being at the situs of the stone to pulverize it. For example, in U.S. Pat. No. 4,679,558 (Nash et al.), assigned to the same assignee of this invention, there is disclosed and claimed a catheter having a working head located at its distal end. The working head is a rotary member arranged to be rotated at a high speed to repeatedly engage the stone to mechanically, e.g., pulverize, it.

In U.S. Pat. 4,811,735 (Nash et al.), also assigned to the same assignee of this invention and whose disclosure is also incorporated by reference herein, there is disclosed and claimed an improved catheter and method of use for disintegrating or otherwise destroying a stone. That catheter also basically comprises a small diameter instrument with a working head located at the distal end thereof. The working head of that instrument comprises a bladed member having at least one impacting surface arranged to be moved from a retracted position, wherein the impacting surface is located adjacent the periphery of the catheter, to an extended position, wherein the impacting surface extends substantially beyond the periphery of the catheter. The working head is arranged to be rotated at a high speed about the longitudinal axis of the catheter when the impacting surface is extended so that the impacting surface repeatedly impacts the stone to disintegrate or otherwise destroy it. Moreover, the rotation of the working head serves to create a vortex flow in the liquid which is located at the situs of the stone to pull the stone into the rotating impacting surface(s) to expedite the pulverization of the stone. A shroud is provided about the distal end of the catheter to aid in directing the stone to the rotating blade while also protecting adjacent body tissue from being engaged by the rotating blade.

In U.S. patent application Ser. No. 07/322,754 filed on Mar. 23, 1989, now U.S. Pat. No. 5,002,549, entitled Stone Pulverizing Apparatus With Improved Working Head And Method Of Use, which is assigned to the same assignee as this invention and whose disclosure is incorporated by reference herein, there is disclosed yet a further improvement in a stone destroying instrument, e.g., catheter, and its method of use. In accordance with one aspect of that invention the catheter utilizes a rotary working head comprising at least two radially extending, blade-like members. Each blade-like member includes plural force-concentrating impacting surfaces and interposed grooves. The rotation of the working head produces a flow of the liquid in which the stone is located past the working head, with some portion of the liquid flowing through the plural grooves. The fluid flowing through the grooves reduces any boundary layer effect which would tend to sweep smaller particles away from the impacting surfaces. Accordingly, the efficient pulverization of the particles and the destruction of the stone is effected.

The revascularization of arteries, ducts, or lumens is another area in which non-invasive procedures are undergoing serious attention, and several patents and patent applications are directed to effecting such action via the use of small diameter instruments having rotary working heads. For example, in U.S. Pat. No. 4,700,705 (Kensey et al.), assigned to the same assignee as this invention, and whose disclosure is incorporated by reference herein, there is disclosed and claimed catheters and methods of use for effecting the opening of a vessel, duct or lumen, such as the opening of a atherosclerotic restriction (partial or total occlusion) in an artery. Those catheters basically comprise of elongated flexible members arranged to be readily passed through the body of the patient to the situs of the procedure to be accomplished, e.g., the location of the atherosclerotic plaque in the artery to be opened. A working head is mounted at the distal end of the catheter and is arranged for high-speed rotation about the longitudinal axis of the catheter. Preferably the catheter is arranged to eject a liquid at the working head to expedite the procedure.

In U.S. Pat. No. 4,747,821 (Kensey et al.), also assigned to the same assignee as this invention and whose disclosure is incorporated by reference herein, there is disclosed and claimed other catheters particularly suited for revascularization of arteries. Each of those catheters includes a rotary working head having at least one non-sharp impacting surface to effect material removal without cutting. The working head is rotated about the longitudinal axis of the catheter at a high rate of speed, e.g., from 10,000 rpm to 200,000 rpm. At the same time, a liquid is passed through the catheter and out of its distal end adjacent the working head to expedite the restriction opening procedure. The opening of the restriction to allow freer flow of blood is effected by the dilation and/or selective emulsification properties of the catheter's working head. In this connection, during the rotation of the working head the liquid jets exiting the distal end of the catheter at the working head are immediately accelerated laterally by portions of the working head so that they are broken up into small segments that develop considerable momentum as they are flung out in all directions, including radial directions, toward the wall of the artery. These liquid segments transfer their momentum to the artery wall, forcing the artery wall outward laterally in all directions, thereby aiding in dilating it.

Moreover, the radial pressure developed by the rotating working head is substantial and can raise local static pressure immediately adjacent the working head by approximately 100 to 200 millimeters of Hg. This increased pressure on the artery wall contiguous with the rotating working head is not due solely to the impact of the liquid segments thereon, but also due to the recirculation of the liquid surrounding the working head. In this connection, the rotation of the working head produces a powerful, toroidal shaped vortex contiguous with the working head. The vortex, in addition to augmenting the application of increased pressure to the artery wall contiguous with the working head, also has the effect of recirculating any particles that may have been broken off from the material forming the arterial restriction by the impact of the rotary working head with that material. In particular the working head, with its non-sharp impacting surfaces differentiates atherosclerotic tissue from normal tissue through the inherent differences in the tissues' physical properties and organizational patterns. Therefore, when the catheter is passed transluminally through the diseased artery, its working head serves to emulsify occlusive lesions not covered with fibrous plaque by repeatedly impacting the material forming the restriction as the working head is rotated, and with minimal risks of puncture or perforation of the contiguous artery wall.

The emulsification process is accomplished by the repeated impaction of the non-sharp impacting surfaces on the material forming the restriction. This action causes the material to be broken away in small particles. The vortex flow at the working head insures that any particles produced by the impacting action are drawn back into contact with the impacting surfaces of the rotating working head. Accordingly, those particles are repeatedly impacted over and over, with each impaction reducing the size of the particles further until the resulting particle size is sufficiently small, e.g., most particles have a surface area less than that of a red-blood cell, that they can be permitted to flow to downstream tissue without causing any significant deleterious effects to the patient.

In U.S. patent application Ser. No. 07/395,109 filed on Aug. 17, 1989, now U.S. Pat. No. 5,042,984, Working Head Having Selectable Impacting Surfaces, which is assigned to the same assignee as this invention and whose disclosure is incorporated by reference herein there is disclosed and claimed catheters whose working heads include impacting surfaces of differing aggressiveness which may be selectively brought into engagement with the restriction to be opened. Such catheters also make use of exiting jets of liquid as described heretofore.

In U.S. patent application Ser. No. 07/395,371 filed on Aug. 17, 1989, now abandoned, entitled Catheter With Expandable Working Head And Method of Use, which is assigned to the same assignee as this invention and whose disclosure is incorporated by reference herein there is disclosed and claimed catheters whose working heads can be increased in size, as desired, to extend their impacting surfaces further outward radially. Such catheters also make use of exiting jets of liquid as described heretofore.

Other catheters for enlarging an opening in a vessel, duct or lumen have been disclosed and claimed in the following United States patents, assigned to the same assignee of this invention, and whose disclosures are also incorporated by reference herein: U.S. Pat. Nos. 4,589,412 (Kensey); 4,631,052 (Kensey), 4,686,982 (Kensey et al.), 4,749,376 (Kensey et al.) and 4,790,813 (Kensey).

It is desirable to ensure that the foregoing types of instruments using rotary driving mechanisms be rendered inoperative after one use to preclude their reuse since such devices may not be capable of assured resterilization, e.g., autoclaving, after they have been used. Moreover, repetitive reuse may result in component failure and hence danger to the patient.

Heretofore, the prior art has provided some devices and/or techniques for ensuring that medical equipment is not reused. Examples of such prior art is found in U.S. Pat. Nos.: 3,597,582 (Goode et al), 3,757,779 (Rovinski), 3,850,348 (Bessot et al), 3,982,538 (Sharpe), 4,226,236 (Genese), and 4,781,683 (Wozniak et al). However, those patents have not provided any viable means for ensuring that instruments utilizing moving working heads driven by rotary drive systems cannot be reused.

OBJECTS OF THE INVENTION

Accordingly, it is the general object of this invention to provide medical apparatus which overcomes the disadvantages of the prior art.

It is a further object of the instant invention to provide minimally invasive medical apparatus for effecting some procedure within the body of a living being yet which apparatus cannot be reused.

It is still a further object of this invention to provide minimally invasive medical apparatus for effecting some procedure within the body of a living being and which apparatus includes means which automatically render it inoperable after its use.

It is a yet further object of this invention to provide minimally invasive medical apparatus for effecting some procedure within the body of a living being and which apparatus includes means which is simple in construction yet effective for automatically rendering the apparatus inoperable after use.

SUMMARY OF THE INVENTION

These and other objects of the instant invention are achieved by providing apparatus for use within the body of a living being to effect some medical procedure therein. The apparatus comprises a tubular member, a working head, drive means, and drive disabling means. The tubular member is arranged to be inserted into the body of the being. The working head, e.g., a rotary stone destroying member, a rotary atherosclerotic plaque removing member, is coupled to the drive means to be operated, e.g., rotated at a high rate of speed, thereby to effect the procedure. The drive means is arranged to be driven, e.g., by a motor coupled thereto. The tubular member carries a liquid, e.g., water, through at least a portion of it during the use of the apparatus. The drive disabling means disables the drive means some time after the liquid is carried through the portion of the member to prevent further operation of the working head.

In one preferred embodiment of the apparatus the drive disabling means comprises a member which changes shape and/or size some time after the liquid is in the tubular member to uncouple the drive means from the motor means.

In another preferred embodiment of the apparatus the drive disabling means comprises a member which changes shape and/or size some time after the liquid is in the tubular member to seize the drive means.

The method of this invention entails performing a procedure within the body of a living being using an apparatus and for disabling the apparatus after one use to prevent its reuse. The method comprises introducing the apparatus into the body of the being, introducing a liquid into the apparatus and carrying the liquid through at least a portion of the tubular member, operating the drive means to effect its movement to cause the working head to effect the procedure. The drive disabling means is operated to disable the drive means some time after the liquid is carried through the portion of the tubular member. This action serves to prevent further use of the apparatus, e.g., operation of its working head.

DESCRIPTION OF THE DRAWINGS

Other objects and many of the attendant advantages of this invention will be readily appreciated as the same becomes better understood by reference to the following detailed description when considered in connection with the accompanying drawings wherein:

FIG. 1 is a longitudinal sectional view, partially broken away, showing one embodiment of an instrument constructed in accordance with this invention prior to being disabled to prevent its reuse;

FIG. 2 is a longitudinal sectional view, partially broken away, showing the embodiment of FIG. 1 after it has been disabled to prevent its reuse;

FIG. 3 is an enlarged sectional view taken along line 3—3 of FIG. 1;

FIG. 4 is a longitudinal sectional view, partially broken away, showing a second embodiment of an instrument constructed in accordance with this invention prior to being disabled to prevent its reuse;

FIG. 5 is a longitudinal sectional view, partially broken away, showing the embodiment of FIG. 4 after it has been disabled to prevent its reuse;

FIG. 6 is an enlarged sectional view taken along line 6—6 of FIG. 4;

DETAILED DESCRIPTION OF THE PREFERRED EMBODIMENT

Figure 7:
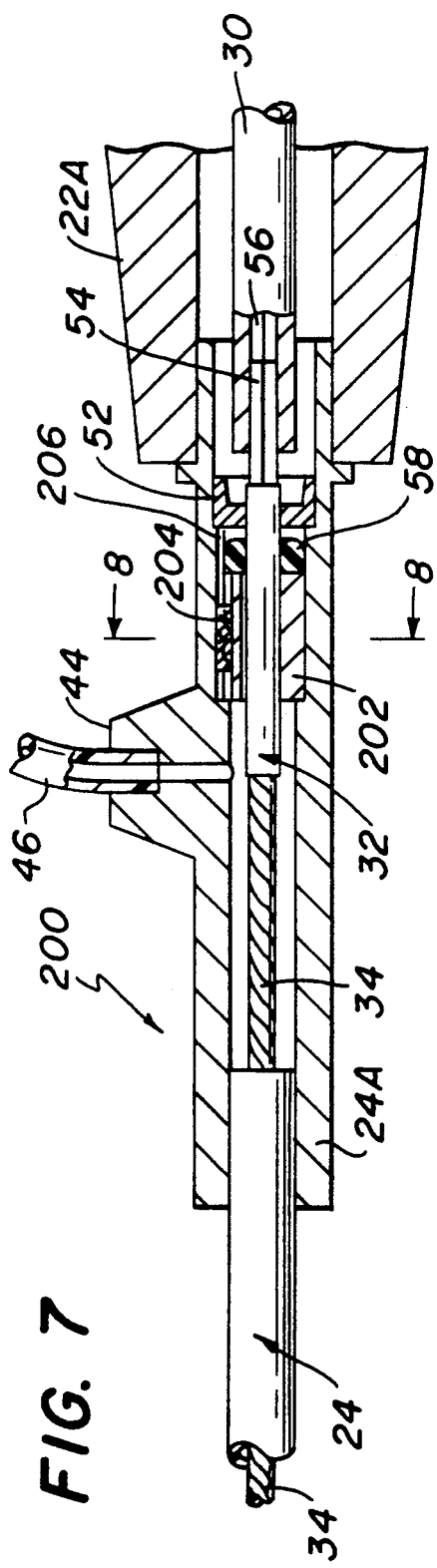
FIG. 7 is a longitudinal sectional view, partially broken away, showing a third embodiment of an instrument constructed in accordance with this invention prior to being disabled to prevent its reuse.

Referring now in detail to the various figures of the drawing wherein like reference characters refer to like parts, there is shown at 20 in FIG. 1 one embodiment of one type of apparatus constructed in accordance with the subject invention. The apparatus 20 is an instrument having a proximally located body portion 22 and a distally located elongated portion 24. The portion 24 is arranged to be disposed within the body of a living being to effect some minimally invasive procedure therein, e.g., a percutaneous, mechanical cholecystotomy, that is, the mechanical destruction of one or more stones (not shown) located within the person's gall bladder. Thus, as can be seen the elongated portion 24 is in the form of a catheter assembly basically comprising a coupling or connector 22A, a first small diameter, elongated, tubular member 24B and a second, even smaller diameter, elongated, tubular member 24C.

In the interest of facilitating the placement of the instrument within the body of the patient to the situs of the stone(s) to be destroyed the catheter portions 24B and 24C are preferably flexible. Thus, the members 24A and 24B are formed of any suitable flexible material, e.g., polyurethane. The members 24B and 24C are connected together at a connector 24D so that their hollow interior portions are in communication with each other to provide a central passageway therethrough.

The member 24C has a distal end at which a working head 26 is mounted. The working head is arranged for high speed rotation about the longitudinal axis 28 of the catheter to effect the destruction of the gallstone(s).

The instrument 20 includes a motor (not shown) located within a motor housing 22A forming a portion of the body 22. The motor can be of any suitable type, e.g., electric, pneumatic, or hydraulic, and includes an output shaft 30 which is rotated at a high rate of speed when the motor is operating. The output shaft includes a bore to form a coupling for a drive assembly 32. The details of the drive assembly 32 will be described later. Suffice it for now to state that the drive assembly includes an elongated drive member, e.g., flexible cable, 34 which extends through the central passageway of catheter portion 24 and is connected at its distal end to the working head 26 to effect the high speed rotation of the working head 26 about axis 28 under power provided from the motor when the working head is in the proper position, e.g., located within the patient's gall bladder.

As can be seen in FIG. 1 the coupling 24A is mounted on the distal end of the motor housing 22A and is a tubular member. In particular its proximal end extends into the interior of the motor housing 22A. The coupling serves to releasably connect the proximal end of the catheter 24 to the motor housing 22A. As will be described later once the instrument 20 has been used, its catheter portion 24 and associated working head are automatically disabled, i.e., precluded from being driven by the motor, thereby precluding reuse of the instrument with that catheter portion. The details and operation of the means for preventing such reuse will be described later.

The working head 26 may be of any type, depending upon the procedure to be accomplished by the instrument. Thus, for a gall stone destroying instrument the working head 26 is preferably constructed in accordance with teachings of the aforementioned U.S. Pat. No. 4,811,735 and patent application Ser. No. 07/322,754. To that end, the working head basically comprises a support hub 36 having a projection centered along the axis of rotation 28 and terminating at a free end portion on which a pair of blades 38 are mounted. Each of the blades 38 is an elongated member having a curved upper surface (not shown) and a planar lower surface (not shown). The blades have the same general shape as an air foil. Each blade includes an elongated linear leading edge and an elongated linear trailing edge. The leading edge of each blade is arranged to repeatedly impact the stone when the working head is rotated to pulverize the stone, and hence result in its destruction.

Each blade 38 is pivotally secured to the support hub to enable it to pivot from a retracted position (not shown) wherein it lies close to the hub to an extended position wherein it extends outward therefrom as shown in FIG. 1. To that end each blade is mounted on a U-shaped member 40 pivotally connected to the hub, so that each member 40 (and the blade mounted thereon) may pivot about a respective transverse axis extending perpendicularly to the axis of rotation 28 and parallel to the sides of the hub. The blades 38 are twisted with respect to each other to form a screw pitch.

When the blades are in the retracted position they lie along respective axes extending generally parallel to and close to the axis of rotation 28 or at a slight outward angle with respect to that axis. As the working head 26 rotates the centrifugal force on the blades causes the blades to pivot outward about the respective transverse axes to the extended position shown in FIG. 1 whereupon the blades extend up to a maximum angle, e.g., 90°, with respect to the axis of rotation. With the blades in this orientation and rotating about axis 28 their screw pitch produces a powerful vortex in the liquid within the gall bladder. This vortex is directed generally inward toward the center of the working head and serves to recirculate the liquid and the stones within the gall bladder into the rotating blades 38 to effect the progressive size reduction (destruction) of the stones.

In accordance with the teachings of the aforementioned patent application Ser. No. 07/322,754 each of the blades includes a plurality of relieved portions or grooves (not shown) in the blade's leading edge. The grooves are of a predetermined width, e.g., 0.5 mm, and are equidistantly spaced along the blades, e.g., at 0.5 mm spacing. The leading edge of each blade is sharp, hence a point-like impacting surface (not shown) is produced at the junction of the leading edge with each side of a groove. These plural point impacting surfaces form what can be termed a line contact fracturing device which is quite efficient in breaking up or pulverizing the stone and its resulting particles without increasing the liquid flow rate (which action could result in tissue damage, e.g., hemorrhage, due to the "sand blasting" effects of the particles impacting the gall bladder tissue). In this regard each point contact impacting surface concentrates the impacting force on the stone particle engaged to expedite its breakage into smaller particles. Moreover, the short leading edge portions between the grooves also form line impacting surfaces (not shown). Being of short length the line impacting surfaces also concentrate an impacting force onto the particles engaged thereby.

The grooves in the blades provide relief for the liquid flowing by the blades to result in what may be termed a "scouring" action. The scouring action reduces the boundary layer effect which is created at blades which do not have grooves. Such a boundary layer tends to sweep smaller particles past (away) from the ungrooved blades without impact. The combined effect of the higher stress from the point impact portions and short line impact portions of the blades and the better access to those portions by the stone particles due to the "scouring" action on the boundary layer reduces stone destrition operating time and particle size.

As can be seen in FIG. 1 the distal end of the catheter portion 24B adjacent the working head 26 includes plural apertures 42 (only one of which can be seen) which are in fluid communication with the hollow interior passageway through the catheter portion 24. These apertures provide a means for introducing a suitable liquid into the gall bladder to expedite the stone destruction process, while also serving as entrance portals through which the stone fragments can be extracted by suction through the catheter.

The coupling member 24A includes a hollow projection 44 which forms a liquid inlet/outlet port for the instrument. The port 44 is in fluid communication with the hollow interior of the coupling 24A and with the central passageway in the catheter portion 24. It is through the port 44 that a liquid is introduced into the instrument 20 and through which particles of the stone(s) which have been pulverized are removed during the stone destruction process. To that end a flexible tube or conduit 46 is connected to the port 44. The conduit provides the liquid from means (not shown) into the coupling. That liquid then passes down the hollow passageway of the catheter portion 24 to exit through the apertures 42. The liquid introduced may be of any desired composition to expedite the stone destruction procedure. Preferably a source of vacuum (not shown) is coupled to port 44 to effect the withdrawal of stone particles from the gall bladder through the catheter. In such a case the suction provided onto conduit 46 causes the stone particles which are in the liquid within the gall bladder to flow with that liquid into the apertures 42, down the length of the catheter portion 24 in the proximal direction, through port 44 and into conduit 46 for removal therefrom.

As is known the gall bladder is a hollow, liquid (e.g., bile) filled structure having relative thin tissue walls located immediately adjacent the liver. In order to guide the stones toward the blades, while also protecting the surrounding tissue from being damaged by the rotating blades, the distal end of the catheter 22 may include a shroud/guide assembly in the form of an expandable basket (not shown). When the basket is in its retracted position it is sufficiently compact so that its outside diameter is not substantially greater than that of the catheter itself. This feature facilitates the placement of the catheter into the gall bladder. Once the working head of the catheter is at the desired location the basket is actuated to cause it to expand to its extended position surrounding the blades, whereupon the basket prevents the blades 38 from engaging the fragile tissue walls of gall bladder. In addition, the basket serves to guide the stones drawn towards the blades by vortex flow.

As can be seen clearly in FIG. 1 the drive cable 34 extends centrally through the hollow interior of the catheter portions 24A and 24B. If desired the cable 34 may be supported within the catheter portion 24 by use of some centering/bearing means, One such means is that disclosed in U.S. Pat. No. 4,686,982 entitled "Spiral Wire Bearing for Rotating Wire Catheter", which is assigned to the same assignee as this invention, and whose disclosure is incorporated by reference herein. Even if no such centering/bearing means is utilized the flow of liquid down the interior passageway of the catheter has the effect of centering the cable therein to allow it to rotate freely therein.

The proximal end of cable 34 terminates in an elongated cylindrical connector member 48. The connector member 48 forms another portion of the drive assembly 34 and extends through a hollow bearing sleeve 50 which is mounted within the coupling 24A. The proximal end of the coupling 24A is closed by a cap 52. The cap includes a central opening through which the connector member 48 extends. The cap serves to center the connector member along the central longitudinal axis 28 of the instrument. The proximal end of the connector member 48 terminates in a free end 54 of square cross section. The free end is arranged to be releasably connected to the drive shaft 30. To that end the distal end of drive shaft 30 includes a longitudinally extending bore 56 of square cross section and into which the free end 54 of the connector member 48 extends. Accordingly, when the connector member 48 is connected to the drive shaft 30 of the motor, operation of the motor effects the rotation of the drive assembly and the working head connected thereto.

An O-ring 58 is disposed about the cylindrical portion of member 48 between the proximal end of the bearing sleeve 50 and the cap 52 to serve as a liquid seal, i.e., prevent any liquid within the interior of the catheter portion 24 from exiting through the proximal end of coupling 24A.

In accordance with the teachings of this invention the instrument is arranged so that it can only be used once. To that end, and as mentioned earlier, the instrument includes means which automatically renders it inoperative some time after its use. In accordance with the preferred embodiments of the invention disclosed herein the entire instrument need not be rendered inoperative, only its catheter portion 24. In so doing the motor and associated means can be retained for reuse with a new catheter portion 24, in the interest of economy.

In the embodiment of FIG. 1 the disabling of the catheter is accomplished by means for automatically disconnecting the drive assembly from the motor some time after use of the instrument. In particular, the catheter 24 is arranged to expand longitudinally with respect to the drive assembly, thereby pulling the square free end 54 of the drive cable free from within the bore 56 in the motor drive shaft 30 as shown in FIG. 2. Accordingly, once such action occurs further operation of the motor will not be effective to rotate the drive assembly and the connected working head 26.

The expansion of the catheter can be readily accomplished various ways within the scope of this invention. One particularly effective way is by forming it of a material which expands in the presence of the liquid which is passed through the catheter portion 24 during use of the instrument. For example, it has been determined that polyurethane will automatically expand somewhat in the presence of water (i.e., polyurethane absorbs water to the extent that a 3 foot length expands approximately ¾ inch in 24 hours). Thus, with a catheter portion 24 of the embodiment of FIG. 1 formed of polyurethane and the liquid which is used during the operation of the instrument including water, the catheter will expand linearly some time after the instrument is used. The drive cable 34 is preferably formed of some material, e.g., stainless steel, which is either resistant to expansion in the presence of the liquid or else expands to a much lesser degree than the material of the catheter portion 24 so that when the catheter portion expands longitudinally the drive cable does not, thereby disengaging the drive cable connector 48 from the drive shaft 30.

In FIG. 4 there is shown an alternative embodiment 100 of the instrument of this invention. The instrument 100 is in most respects identical in construction and operation as that of instrument 20. Accordingly, the same reference numerals will be used for the corresponding components and their construction and operation will not be reiterated. However, instrument 100 makes use of considerably different means for preventing reuse of the catheter portion 24. In particular that means basically entails seizing the drive cable 34 some time after use of the instrument to prevent its further rotation rather than uncoupling the drive assembly from the motor as is accomplished by instrument 20.

The cable seizing means of instruments constructed in accordance with this invention, such as instrument 100, can take many forms. In the embodiment shown and described hereinafter that means (like the uncoupling means of the instrument 20) operates in automatic response to the presence of the liquid, e.g., water, through the catheter portion 24.

The cable seizing means of instrument 100 basically comprises a clamp member 102 and an associated prop member 104. The clamp member 102 and associated prop member 104 are disposed within an enlarged diameter passageway in a coupling member 24A'. The coupling member 24A' is identical in virtually all respects to coupling member 24A described heretofore except for the shape of the central passageway extending therethrough. Moreover, as can be seen in FIGS. 4 and 5, the proximal end of the catheter portion 24B is of an enlarged diameter, designated by the reference numeral 24B', and is disposed within an enlarged diameter passageway portion in coupling member 24A'.

As can be seen clearly in FIGS. 4 and 6 the clamp member 102 is of a generally C-shape, formed of a resilient material, e.g., stainless steel, and includes a pair of legs 102A joined together by a central portion 102B. Each leg terminates in a inwardly projecting free end tab 102C. The tabs 102C serve as the means for clamping the cable 34 therebetween to seize the cable and prevent its rotation after one use of the instrument 100. To that end the cable 34 extends between the tabs 102C and legs 102A and through the opening 102D. The prop member 104 is formed of a material, e.g., sugar, gelatin, compressed paper, etc., which softens or dissolves some predetermined time, e.g., from 1 to 20 hours, after being subjected to the liquid, e.g., water, which is used during the operation of the instrument, and is disposed between the legs 102B adjacent the tabs 102C and laterally of the cable 34. The pro member is dimensioned so that when it is interposed between the legs 102B it biases the legs outward to the flared position shown in FIGS. 4 and 6, whereupon the tabs 102C do not engage the cable 34 passing therebetween. The natural resiliency of the clamp member tries to restore the legs to the position shown in FIG. 5 but the existence of the prop member therebetween prevents such action. However, some time after the instrument is used, i.e., liquid is passed through the catheter portion 24, the prop means softens or dissolves, thereby enabling the legs 102A to spring toward each other to the closed position shown in FIG. 5, whereupon the tabs 102C tightly engage the cable therebetween to seize it and prevent further rotation thereof.

In order to ensure that the prop doesn't soften or dissolve prematurely the instrument 100 is preferably assembled in a clean room and packaged in a hermetically sealed, moisture resistent package.

In FIG. 7 there is shown another alternative embodiment 200 of an instrument of this invention. The instrument 200 is in most respects identical in construction and operation as that of instrument 20. Accordingly, the same reference numerals will be used for the corresponding components and their structure and operation will not be reiterated. However, like the instrument 100, the instrument 200 makes use of means for seizing the drive cable 34 some time after use of the instrument to prevent its further rotation rather tha uncoupling the drive assembly from the motor as is accomplished by instrument 20.

The cable seizing means of instrument 200 also operates in automatic response to the presence of the liquid, e.g., water, through the catheter and basically comprises a split bearing bushing 202 and an associated expansion member 204. The construction of expansion member will be described later. Suffice it for now to state that the bearing bushing is formed of any suitable material, e.g., wood, which expands in the presence of the liquid, e.g., water, which is used in the catheter when the instrument is operated.

Figure 9:
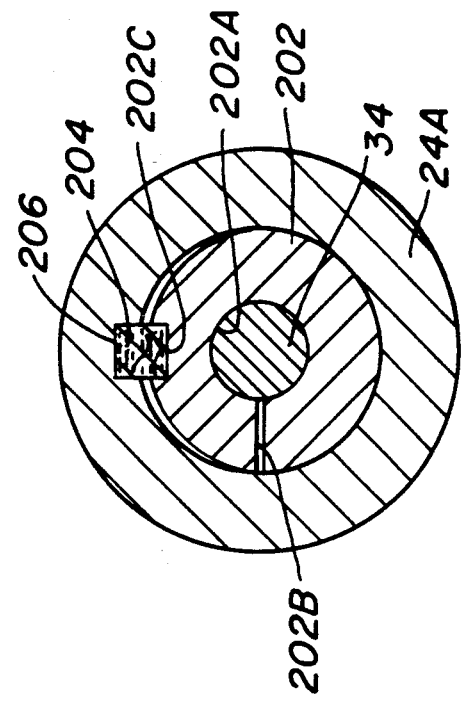
FIG. 9 is an enlarged sectional view like that of FIG. showing the embodiment of FIG. 7 after it has been disabled to prevent its reuse.
Figure 8:
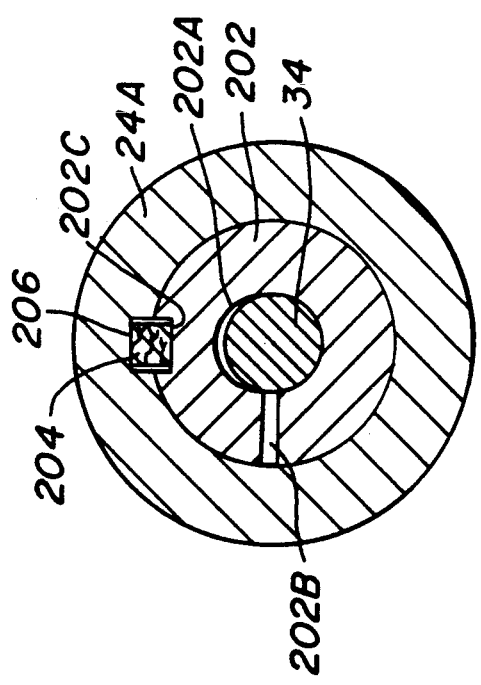
FIG. 8 is an enlarged sectional view taken along line 8—8 of FIG. 7.

As can be seen in FIGS. 7-9 the bushing basically comprises an elongated tube or sleeve having a central passageway 202A extending longitudinally the entire length of the bushing and a longitudinally extending gap 202B communicating with the passageway 202A and also extending the entire length of the bushing. The cable 34 extends through the passageway 202A and is generally centered thereby.

In accordance with a preferred embodiment of this invention the bushing 202 is formed of any suitable resilient material, e.g., metal, plastic, etc., so that it is normally open, i.e., the gap 202B is open, like that shown in FIG. 8. This feature ensures that the cable is loosely disposed within the passageway 202A and free to rotate about its longitudinal axis therein. The bushing 202 also includes a linear slot 202C extending longitudinally along the bushing's outer surface. A similar slot 206 is provided in the interior of the coupling member 24A and is disposed opposite to the slot 202C when the bushing 202 is located within the coupling member. The expansion member 204 comprises an elongated member of generally square cross section and which is configured so that when it is in its unexpanded state it fits within the opposed slots 206 and 202C so that the bushing is in its open state (like that of FIG. 8). However, since the member 204 is expandable in the presence of liquid, some time after use of the instrument, i.e., passage of liquid through the catheter portion 24, the member 204 will expand in cross section to the state shown in FIG. 9, whereupon it biases or crushes the split bushing to its closed state. This action effects the seizure of the cable within the passageway 202A, whereupon further rotation of the cable is precluded.

In order to ensure that the expansion member 204 doesn't expand prematurely the instrument is also preferably assembled in a clean room and packaged in a hermetically sealed, moisture resistent package.

It should be pointed out at this juncture that other means. for disabling the drive system can be utilized in lieu of the uncoupling means of instrument 20 or the cable seizing means of instruments 100 and 200. Thus, apparatus constructed in accordance with this invention may make use of some means for automatically severing the cable or some portion of the drive system some time after use of the apparatus.

It should also be pointed out that the disabling of the apparatus after one use need not occur in automatic response to the presence of the liquid within the catheter, but can occur in response to some other condition or state of the instrument which only occurs during the first actual use of the instrument. The use of means responsive to the presence of liquid within the catheter in the preferred embodiments as disclosed herein has been selected since it serves as a convenient and assured way of disabling the apparatus after its first actual use (and not its testing which may occur before actual use). In this regard the instrument may be tested without use of the liquid, but is not used for performing the desired procedure, e.g., stone destruction, artery revascularization, etc., without the use of that liquid.

Without further elaboration, the forgoing will so fully illustrate my invention that others may, by applying current or future knowledge, readily adopt the same for use under various conditions of service.

What is claimed is:

1. Apparatus for use within the body of a living being, said apparatus comprising a tubular member, a working head, drive means, and drive disabling means, said tubular member being of small cross-sectional area to enable it to be inserted in the body of said being, said working head located adjacent said tubular member and being coupled to said drive means to be operated thereby to effect some procedure within said body, said drive means being arranged to be driven by motor means coupled thereto, said tubular member carrying a liquid through at least a portion thereof, said drive disabling means disabling said drive means some time after said liquid is carried through said portion of said member to thereby prevent operation of said working head.

2. The apparatus of claim 1 wherein said drive means comprises a first member extending through said tubular member and arranged to be moved by said motor means.

3. The apparatus of claim 2 wherein said first member is arranged to be rotated by said motor means.

4. The apparatus of claim 3 wherein said drive disabling means is arranged to sense the presence of lqiuid through said tubular member and to automatically prevent the rotation of said first member some time after sensing said liquid.

5. The apparatus of claim 4 wherein said drive disabling means changes size in automatic response to the presence of liquid.

6. The apparatus of claim 5 wherein said drive disabling means comprises an engagement member which expands in the presence of liquid and is located adjacent a portion of said drive means to engage and seize a portion thereof to preclude rotation fo said first member.

7. The apparatus of claim 6 wherein said tubular member is elongated and includes a portion which is flexible.

8. The apparatus of claim 5 wherein said drive disabling means comprises at least a portion of said tubular member which expands in the presence of liquid to uncouple said drive means from said motor means to preclude rotation of said first member.

9. The apparatus of claim 8 wherein said tubular member is elongated and includes a portion which is flexible.

10. The apparatus of claim 4 wherein said disabling means changes shape in automatic response to the presence of fluid.

11. The apparatus of claim 2 wherein said drive disabling means is arranged to sense the presence of liquid through said tubular member and to automatically prevent the movement of said first member some time after sensing said liquid.

12. The apparatus of claim 11 wherein said drive disabling means changes size in automatic response to the presence of liquid.

13. The apparatus of claim 12 wherein said drive disabling means comprises an engagement member which expands in the presence of liquid and is located adjacent a portion of said drive means to engage and seize a portion thereof to preclude movement of said first member.

14. The apparatus of claim 12 wherein said drive disabling means comprises at least a portion of said tubular member which expands in the presence of liquid to uncouple said drive means from said motor means.

15. The apparatus of claim 11 wherein said drive disabling means changes shape in automatic response to the presence of fluid.

16. The apparatus of claim 1 wherein said tubular member is elongated and includes a portion which is flexible.

17. A method of performing a procedure within the body of a living being using an apparatus and for disabling said apparatus after one use to prevent its reuse, said apparatus comprising a tubular member, a working head, motor driven, drive means, and drive disabling means, said method comprisign introducing said apparatus into the body of said being, introducing a liquid into said apparatus and carrying said liquid through at least a portion of said tubular member, operating said drive means to effect its movement to cause said working head to effect said procedure, and causing said drive disabling means to disable said drive means some time after said liquid is carried through said portion of said member to thereby prevent further operation of said working head.

18. The method of claim 17 wherein said drive disabling means. automatically disables said drive means after said some time.

19. The method of claim 18 additionally comprising sensing the presence of liquid through said tubular member, whereupon said drive disabling means automatically prevents the operation of said working head after said some time.

20. The method of claim 19 wherein said drive disabling means changes size in automatic response to the presence of liquid.

21. The method of claim 20 wherein said drive disabling means comprises an engagement member which expands in the presence of liquid and is located adjacent a portion of said drive means to engage and seize a portion thereof to preclude its movement.

22. The apparatus of claim 20 wherein said apparatus additionally comprises motor means releasably coupled to said drive means, and wherein said drive disabling means comprises at least a portion of said tubular member which expands in the presence of said liquid to uncouple said drive means from said motor means to preclude movement of said drive means.

23. The method of claim 19 wherein said drive disabling means changes shape in automatic response to the presence of fluid.

* * * * *